United States Patent [19]

Dettwiler et al.

[11] Patent Number: 5,330,495
[45] Date of Patent: Jul. 19, 1994

[54] DISPOSABLE GRAFTING KNIFE

[75] Inventors: Daniel R. Dettwiler, Vacaville; Michael D. Shannon, Fairfield, both of Calif.

[73] Assignee: The United States of America as represented by the Secretary of the Air Force, Washington, D.C.

[21] Appl. No.: 65,795

[22] Filed: May 24, 1993

[51] Int. Cl.$^5$ .............................................. A61B 17/32
[52] U.S. Cl. ..................................... 606/167; 606/132
[58] Field of Search ............... 606/167, 161, 133, 160, 606/131, 132; 30/280, 281; 128/757

[56] References Cited

U.S. PATENT DOCUMENTS

| | | | |
|---|---|---|---|
| 3,797,505 | 3/1974 | Gilhaus et al. | 606/132 |
| 3,934,591 | 1/1976 | Gleason | 606/132 |
| 4,038,986 | 8/1977 | Mahler | 606/132 |
| 4,221,222 | 9/1980 | Detsch | 606/132 |
| 4,735,202 | 4/1988 | Williams . | |
| 5,055,106 | 10/1991 | Lundgren . | |
| 5,078,724 | 1/1992 | Takase . | |
| 5,139,507 | 8/1992 | Dolgin et al. . | |
| 5,156,607 | 10/1992 | Kansas . | |
| 5,183,053 | 2/1993 | Yeh et al. . | |

FOREIGN PATENT DOCUMENTS 1192654  5/1970  United Kingdom ................ 606/160

OTHER PUBLICATIONS

Rateitschak et al, Color Atlas of Dental Medicine, vol. 1 "Periodontology" (1989).

Primary Examiner—Stephen C. Pellegrino
Assistant Examiner—William W. Lewis
Attorney, Agent, or Firm—Bobby D. Scearce; Thomas L. Kundert

[57] ABSTRACT

A disposable gingival grafting knife is described which comprises a narrow blade sharpened on one side, formed to define a preselected cross-sectional shape of the graft and embedded into the end of a sterilizable handle to define preselected width and thickness for the graft, and a tissue graft receptacle removably attachable to the back of the knife near the blade for catching the harvested graft.

8 Claims, 2 Drawing Sheets

DISPOSABLE GRAFTING KNIFE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to surgical instruments and more particularly to a disposable gingival grafting knife.

Conventional gingival grafting methods require a scalpel and a unigraft knife or motor-driven mucotome to harvest a graft. Using a scalpel is excessively time consuming and often provides uneven graft width and thickness. Use of a unigraft knife or mucotome is expensive and carries a substantial risk of cross contamination.

The invention solves or substantially reduces in critical importance problems with prior art instruments and methods by providing a disposable sterilizable gingival grafting knife which can be used to easily and effectively harvest a graft of uniform width and thickness and be discarded safely and cost effectively without risk of cross contamination. The invention comprises a narrow blade, sharpened on one side, formed to the desired shape of the graft and embedded into the end of a handle to define preselected width and thickness for the graft. A detachable tissue graft receptacle is attachable to the back of the knife near the blade for catching and holding the harvested graft.

The invention is ideal for soft tissue grafts and is valuable to dentists, periodontists, oral surgeons and implantologists.

It is therefore a principal object of the invention to provide an improved surgical knife.

It is another object of the invention to provide a surgical instrument for harvesting a tissue graft of uniform width and thickness.

It is a further object of the invention to provide a disposable periodontal knife.

These and other objects of the invention will become apparent as a detailed description of representative embodiments proceeds.

SUMMARY OF THE INVENTION

In accordance with the foregoing principles and objects of the invention, a disposable gingival grafting knife is described which comprises a narrow blade sharpened on one side, formed to define a preselected cross-sectional shape of the graft and embedded into the end of a sterilizable handle to define preselected width and thickness for the graft, and a tissue graft receptacle removably attachable to the back of the knife near the blade for catching the harvested graft.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
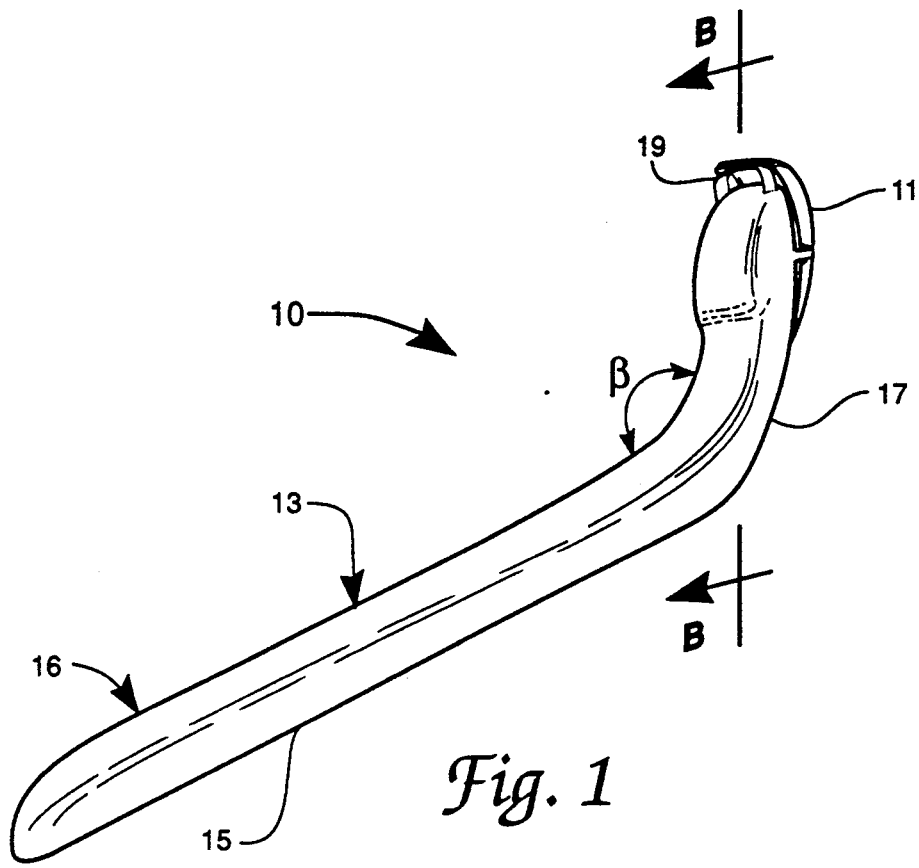
FIG. 1 is a perspective view of a grafting knife representative of the invention including assembly of the tissue receptacle.
Figure 1A:
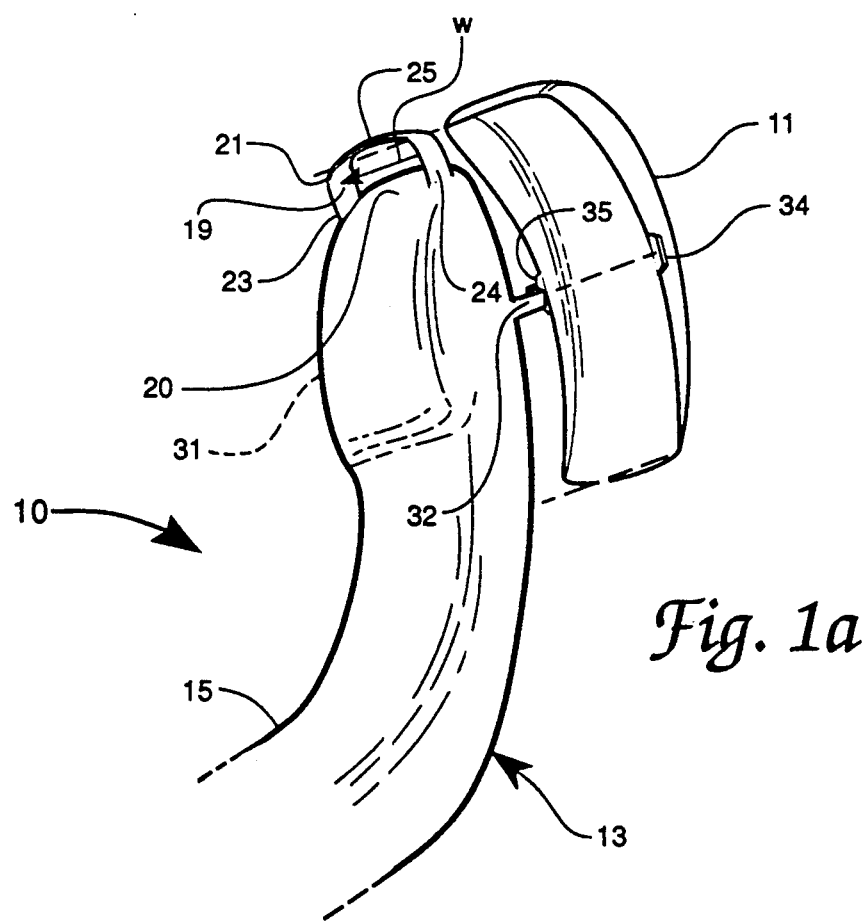
FIG. 1a is a partial perspective view of the blade end of the FIG. 1 knife showing the tissue receptacle detached from the knife portion.
Figure 2:
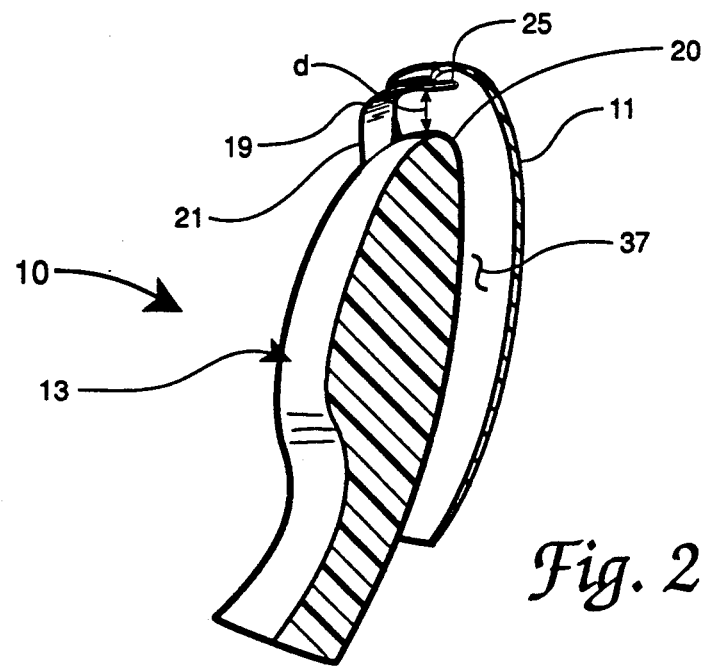
FIG. 2 is a sectional view of the assembled knife and receptacle as viewed along line B—B of FIG. 1.

Referring now to the drawings, FIG. 1 is a perspective view of grafting knife 10 representative of the invention, with tissue graft receptacle 11, discussed more fully below, attached to knife portion 13. FIG. 1a shows in perspective the blade end of knife 10 with receptacle 11 detached from knife portion 13. FIG. 2 shows a sectional view of assembled knife portion 13 and receptacle 11 as viewed along line B—B of FIG. 1. Knife portion 13 comprises handle 15 of suitable material formed into the configuration as shown, including first lengthwise portion 16 sized for ease of grasping by the user of knife 10, and second lengthwise portion 17 supporting blade 19 embedded at distal end 20 of handle 15. Second portion 17 is disposed to first portion 16 at angle $\beta$ (about 120° to 150°, preferably 135°) preselected to facilitate harvesting a tissue graft as discussed below in relation to FIG. 3. Handle 1 comprise any suitable formable material sufficiently resistant to conventional sterilization (e.g., Chemiclave at about 270° F. and 20–40 psi; Autoclave at about 250° F. and 15–18 psi), as would occur to the skilled artisan guided by these teachings, such as acrylic or Plexiglas ™. In a model built in demonstration of the invention, handle 15 was fabricated of light-cured acrylic and was about 4.5 inches in overall length and tapered over the length to a width of about 3/8 inch at end 20.

Referring additionally to FIG. 2, blade 19 has sharpened edge 21 and the preselected shape suggested in the figures, with corresponding ends 23,24 embedded into opposite sides of handle 15 at end 20. Blade 19 shape defines a preselected width w and spacing d between end 20 and central portion 25 of blade 19. In using knife 10 to harvest a tissue graft as discussed below, w and d define intended width and thickness of the graft; although graft size is not considered limiting of the invention, w usually is in the size range of about 5 to 9 mm and d usually is in the size range of about 1.0 to 1.5 mm for most periodontal, dermatologic, burn therapy or other type grafts. Blade 19 may be any suitable width ($\sim 2$ mm in the demonstration model) and comprises any suitable material such as surgical steel, stainless steel, razor blade material or carbide steel, as is used conventionally for surgical instruments.

Knife 10 may include optional cup-shaped tissue graft receptacle 11 detachably mounted to second portion 17 near blade 19. Receptacle 11 is attachable to handle 15 by any suitable means such as a pair of tabs 31,32 on opposite sides of handle 15 received by corresponding slots or tabs 34,35 on opposite sides of receptacle 11. Receptacle 11 defines cavity 37 for receiving a harvested graft and therefore prevents aspiration of the graft by a suction device used in conjunction with treatment of the patient or inadvertent swallowing of the graft by the patient, and minimizes the number of instruments needed for a harvesting procedure.

Figure 3:
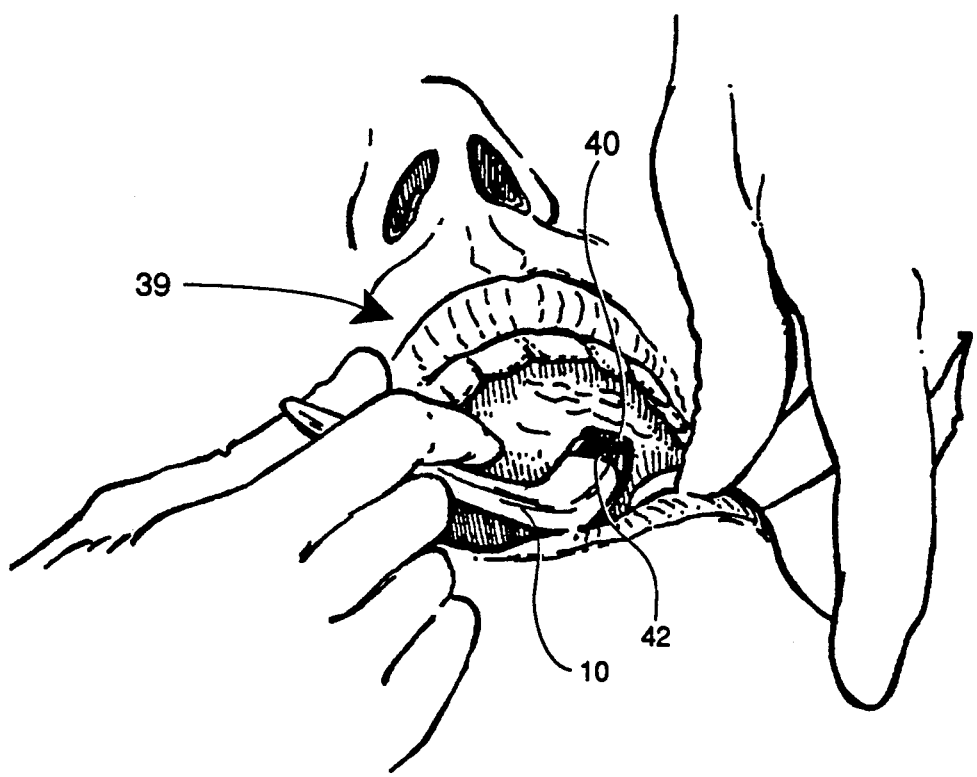
FIG. 3 is a sketch of a palate of a patient illustrating the harvesting of a tissue graft therefrom using the invention.

FIG. 3 is a sketch of the palate of a patient 39 illustrating the convenient use of the invention to harvest a graft of palatal keratinized tissue and subjacent connective tissue. As suggested above, a graft of about 1.5 mm thickness may be normally taken. A scalpel (not shown) is first used to make a small incision 40 (1 cm or less in width) posteriorly away from the marginal tissue. Blade 19 of knife 10 is then inserted into incision 40 and drawn anteriorly for the desired graft 42 length. The harvested tissue graft 42 may then be approximated and sutured at a recipient site. Knife 10 may then be discarded. The invention was successfully tested to harvest free gingival grafts of uniform width and thickness from the palate of sheep bioheads for placement on the mandibular anterior teeth. The invention was also tested on a human patient to harvest a gingival graft (8 mm wide by 1.5 to 2.0 mm thick) from the palate for placement on the mandibular anterior teeth 23-25.

The invention therefore provides a novel disposable grafting knife. It is understood that modifications to the invention may be made within the scope of the appended claims as might occur to one with skill in the field of the invention. All embodiments contemplated hereunder which achieve the objects of the invention have therefore not been shown in complete detail. Other embodiments may be developed without departing from the spirit of the invention or from the scope of the appended claims.

We claim:

1. A disposable surgical knife for harvesting a tissue graft of substantially uniform width and thickness, comprising:
    (a) a handle having first and second ends and corresponding first and second lengthwise portions of respective preselected lengths joined at an angle of about 120° to 150°;
    (b) a narrow blade having first and second ends, said blade being sharpened on one side and formed along the length thereof to define a preselected cross-sectional size and shape of a tissue graft, said first and second ends of said blade being embedded into said second end of said handle to define preselected width and thickness for said cross-sectional size and shape of the graft; and
    (c) a cup-shaped receptacle removably attachable to said second lengthwise portion of said handle near said blade, said receptacle defining a cavity near said blade for catching a harvested tissue graft, and means on said handle near said second end thereof for removably attaching said receptacle to said handle.

2. The knife of claim 1 wherein said angle is 135°.

3. The knife of claim 1 wherein said blade comprises surgical steel, razor blade material, stainless steel or carbide steel.

4. The knife of claim 1 wherein said handle is a sterilizable material selected from the group consisting of Plexiglas TM and acrylic.

5. A disposable surgical knife for harvesting a tissue graft of substantially uniform width and thickness, comprising:
    (a) a handle having first and second ends and corresponding first and second lengthwise portions of respective preselected lengths joined at an angle of about 120° to 150°;
    (b) a narrow blade having first and second ends, said blade being sharpened on one side and formed along the length thereof to define a preselected cross-sectional size and shape of a tissue graft, said first and second ends of said blade being embedded into said second end of said handle to define preselected width and thickness for said cross-sectional size and shape of the graft;
    (c) a cup-shaped receptacle attached to said second lengthwise portion of said handle near said blade, said receptacle defining a cavity near said blade for catching a harvested tissue graft; and
    (d) means on said handle near said second end thereof for attaching said receptacle to said handle.

6. The knife of claim 5 wherein said angle is 135°.

7. The knife of claim 5 wherein said blade comprises surgical steel, razor blade material, stainless steel or carbide steel.

8. The knife of claim 5 wherein said handle is a sterilizable material selected from the group consisting of Plexiglas TM and acrylic.

* * * * *